United States Patent [19]
Menzel

[11] Patent Number: 5,241,184
[45] Date of Patent: Aug. 31, 1993

[54] APPARATUS AND METHOD FOR QUANTIZING REMAINING LIFETIME OF TRANSMISSION CABLE INSULATION

[75] Inventor: Erhard R. Menzel, Lubbock, Tex.

[73] Assignee: Electric Power Research Institute, Palo Alto, Calif.

[21] Appl. No.: 766,653

[22] Filed: Sep. 26, 1991

[51] Int. Cl.$^5$ .......................................... G01N 21/64
[52] U.S. Cl. ............................. 250/458.1; 250/459.1
[58] Field of Search ............. 250/458.1, 459.1, 461.1, 250/362, 302

[56] References Cited

U.S. PATENT DOCUMENTS

| | | | |
|---|---|---|---|
| 4,345,840 | 8/1982 | Goetz et al. | 250/340 |
| 4,476,870 | 10/1984 | Peterson et al. | 250/458.1 |
| 4,791,293 | 12/1988 | Barriere | 250/458.1 |
| 4,802,762 | 2/1989 | Hill, Jr. | 250/459.1 |
| 4,880,972 | 11/1989 | Brogardh et al. | 250/458.1 |
| 4,894,547 | 1/1990 | Leffell et al. | 250/459.1 |
| 4,895,156 | 1/1990 | Schulze | 250/458.1 |
| 4,988,875 | 1/1991 | Ortiz et al. | 250/359.1 |
| 4,992,666 | 2/1991 | Robertson | 250/461.1 |
| 5,070,248 | 12/1991 | Pesce | 250/483.1 |
| 5,108,932 | 4/1992 | Wolfbeis | 250/458.1 |

FOREIGN PATENT DOCUMENTS 0103943  5/1988  Japan ................................ 250/458.1

OTHER PUBLICATIONS

326/SPIE, vol. 871 (1988) Space Structures, Power and Power Conditioning, paper entitled *Surface Breakdown of Pre-Stressed Insulators*, by L. L. Hatfield, V. K. Agarwal, and E. R. Menzel, pp. 326-332.

Appl. Phys. Lett. 49 (24) Dec. 15, 1986 0003-6951/86/501638-03, *Fluorescence Probes for Study of Insulator Damage*, by E. R. Menzel, L. L. Hatfield, and V. K. Agarwal, pp. 1638-1640.

60/SPIE vol. 743, Fluorescence Detection (1987), *Fluorescence Probes for Study of Damage in Dielectrics*, by E. R. Menzel, L. L. Hatfield, V. K. Agarwal, et al, pp. 60-67.

Annual Report I.E.E.E. (1987), p. 519, *Laser Excited Fluorescence Probes to Study Insulator Damage*, by D. J. Zoledziowska, E. R. Menzel, V. K. Agarwal, L. L. Hatfield, pp. 519-525.

Seventh Proc. I.E.E.E. (1989), p. 816, *Laser-Excited Fluorescence Probes for Surface Flashover Studies of the Insulator Celcon*, by D. J. Zoledziowska, E. R. Menzel, and L. L. Hatfield, pp. 816-819.

*Primary Examiner*—Carolyn E. Fields
*Assistant Examiner*—Drew A. Dunn
*Attorney, Agent, or Firm*—Flehr, Hohbach, Test, Albritton & Herbert

[57] ABSTRACT

The remaining life of transmission cable insulation is quantized by irradiating the insulation with excitation energy causing it to emit a bulk fluorescence spectrum. The intensity of the bulk fluorescence spectrum is then measured at at least two wavelengths and an intensity ratio determined at these wavelengths. The magnitude of the resultant ratio correlates with the age and condition of the insulation under test, and allows estimation of the remaining transmission cable insulation lifetime. Such measurements may be made in situ if the transmission cable includes a projecting fiber optic cable having first and second ends. The first end of the fiber optic cable is embedded within the cable so as to touch the insulation, and the second end is adapted to receive energy causing the bulk fluorescence, and is further adapted to optically communicate the bulk fluorescence to an optical measurement system that determines intensities and ratios. In this fashion, the remaining lifetime of insulation within a transmission cable may be estimated, even though the transmission cable remains buried underground.

14 Claims, 3 Drawing Sheets

APPARATUS AND METHOD FOR QUANTIZING REMAINING LIFETIME OF TRANSMISSION CABLE INSULATION

FIELD OF THE INVENTION

This invention relates to transmission cable, and more particularly to a method for quantizing the remaining life of transmission distribution cable insulation, and to a transmission cable facilitating the use of such method.

BACKGROUND OF THE INVENTION

Power transmission distribution cable includes an electrical conductor that is commonly surrounded by a semiconducting polymer, by insulation, and finally by an outer protective jacket. The high potential usually carried by the conductor, and the environment in which the cable is located contribute to deterioration of the cable insulation. If the transmission cable is not replaced before the insulation deteriorates significantly, catastrophic failure and damage can result. Similarly, even transmission cable conducting a lower potential within a radiation environment can cause catastrophic failure if it is not replaced before its insulation deteriorates significantly.

Techniques are known in the art for diagnosing insulation failure after the fact. After failure, the insulation's electrical breakdown characteristics are analyzed to try to learn the mode of failure. Infrared spectroscopic studies of the insulation may be conducted, in addition to analysis of the insulation deterioration (known as "water treeing"). At best, the results of such studies may be useful in learning why the insulation failed.

However there is no known technique whereby cable insulation may be examined, preferably before catastrophic damage, and the remaining insulation lifetime predicted. For example, if the insulation fails in a segment of installed cable, what should be done? If the failure was due to aging, then the entire cable installation should be replaced (since all of the insulation is equally old and will fail soon). On the other hand, if the failure was localized, it would suffice to splice in a new section of cable to replace the failed cable segment. Unfortunately, the prior art does not provide a diagnostic method by which the remaining insulation lifetime may be quantized.

There is a need for a method of predicting the remaining lifetime of transmission cable based upon examination of its insulation. Preferably the method should enable such analysis to be made even when the transmission cable is buried underground, or is within a hostile environment such as a nuclear reactor. The present invention provides such a method. Further, the present invention provides a transmission cable facilitating such analysis, as well as a method for fabricating such cable.

SUMMARY OF THE INVENTION

The present invention uses a spectroscopic analysis of the inherent bulk photoluminescence of transmission cable insulation to estimate the remaining insulation lifetime. An exposed region of insulation is subjected to excitation at a first wavelength chosen to cause the exposed insulation to bulk fluoresce. In response to this excitation, the exposed insulation emits a broad spectrum of longer wavelength photoluminescence having different intensities at different wavelengths. Using conventional spectroscopic equipment, the response spectrum intensity is analyzed at various wavelengths.

Applicant has discovered that a ratio of response spectrum intensities at two different wavelengths correlates well with insulation age and condition, and is an indicia of remaining lifetime of the insulation under test. The two wavelengths are selected according to the type of insulation to best discriminate between potentially good and bad insulation.

In practice, intensity ratios are determined for the insulation in a transmission cable using the above-described method. These ratios are then compared with a table correlating estimated remaining insulation lifetime with intensity ratios for the insulation type under test. The correlation table allows the remaining insulation lifetime to be quantized, and thus facilitates deciding whether to replace the transmission cable.

Although the preferred embodiment is directed to transmission cable insulation whose condition changes with age, exposure to electricity and chemicals in the environment, the disclosed method is applicable to insulated cable in other environments as well. For example, insulation in cable associated with nuclear reactors, accelerator chambers and similar environments is subject to deterioration from radiation. The present invention allows estimation of the remaining insulation lifetime in such cable.

In another aspect, a transmission cable adapted for use with the above method is disclosed. The first end of a fiber optic sensor, such as a fiber optic material, is embedded in the outer protective jacket of a transmission cable, preferably when the cable is manufactured. This first end is embedded just far enough to touch the insulation without actually being embedded in the insulation. The second end of the sensor protrudes from the cable such that sensor access is provided even when the cable is buried, is located in a hostile environment, or is otherwise not readily accessible. A source of first wavelength emission is optically coupled to the second end of the fiber optic sensor, which preferably is disposed for easy access, thereby permitting excitation of the buried cable insulation. Suitable optical measurement equipment, also coupled to the second end of the fiber optic, permits analysis of the broad spectrum of photoluminescence emitted by the insulation. In this fashion, intensity ratios may be determined in the field, and the remaining insulation lifetime estimated without removing the cable from its environment.

Other features and advantages of the invention will appear from the following description in which the preferred embodiments have been set forth in detail in conjunction with the accompanying drawings.

DETAILED DESCRIPTION OF THE PREFERRED EMBODIMENTS

Figure 1:
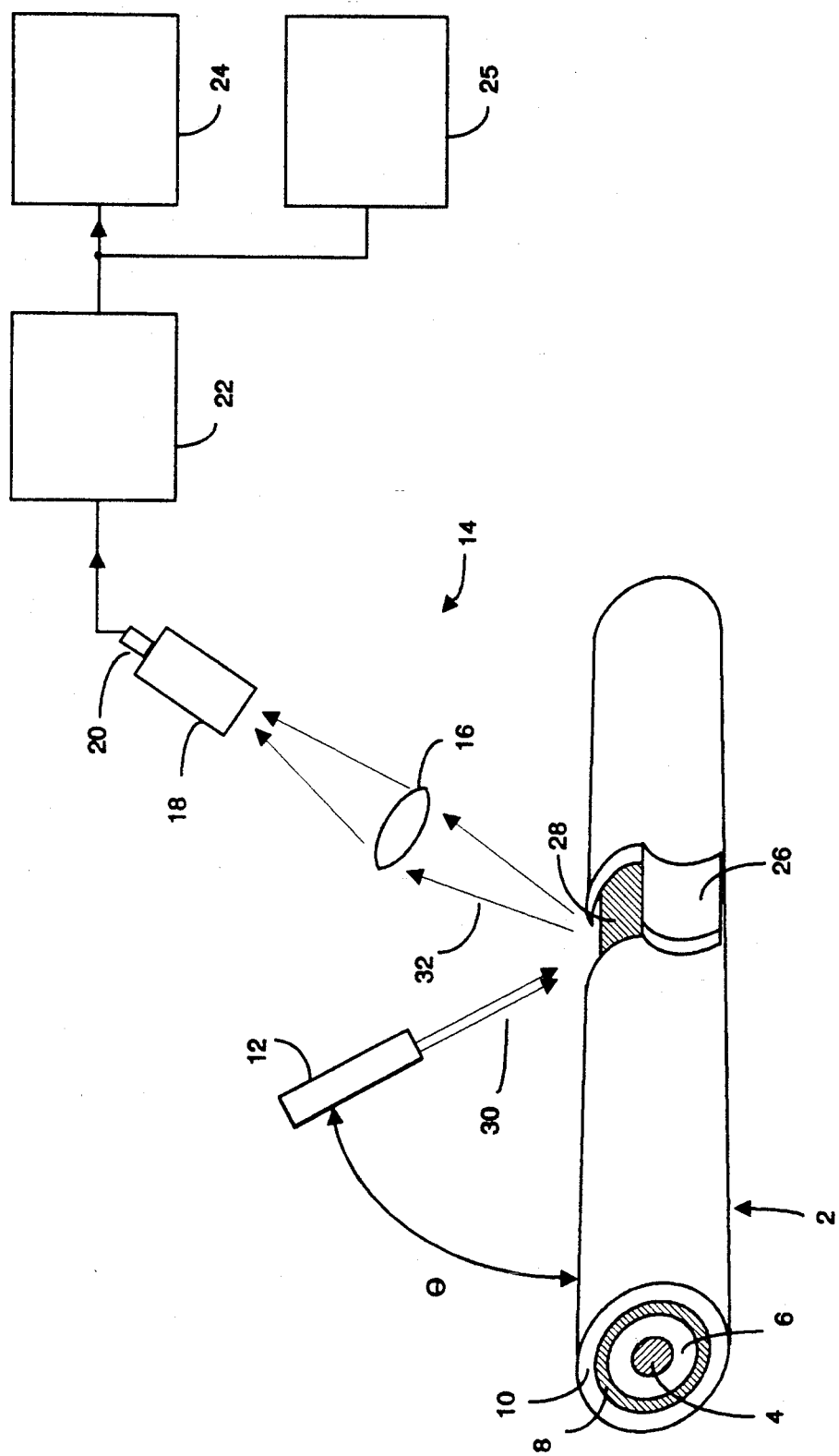
FIG. 1 depicts a method for quantizing remaining transmission cable insulation lifetime according to the present invention.

FIG. 1 shows a section of transmission line cable 2 as including a center conductor 4 (that defines the longitudinal axis of cable 2), axially surrounded by a semiconducting polymer 6, insulation 8, and a protective outer jacket 10. The center conductor 4 carries electricity and for that reason preferably is a low resistance material, e.g., copper or braided aluminum. The semiconducting polymer 6 surrounds the conductor and "smoothes out" the electric field generated by the electricity carried by conductor 4. The insulation 8, toward which this invention is directed, is commonly a cross-linked polyethylene ("XLPE") or ethylene propylene rubber ("EPR") material, although other materials may be used instead. A protective jacket 10 is outermost and, together with the insulation 8, protects the conductor 4 from the environment, and vice versa.

Typically the outer diameter of the cable 2 is about 2.5 cm, and the voltage carried by the conductor 4 can be as high as 9 KV or more. Although denoted "transmission line" cable, cable 2 may also be an insulated cable that carries electricity (including low potential electricity) and signals within a hostile environment, including high radiation environments such as a nuclear reactor, a particle accelerator, and the like.

FIG. 1 further shows an excitation source 12 and an optical measurement system 14 that provides a quantitative analysis of the remaining lifetime of the insulation 8, according to the present invention. The optical measurement system 14 preferably includes a lens 16, a double monochromator 18, a photomultiplier tube 20, a photon counter 22 and a chart recorder 24. Alternatively, the output signals from the photon counter 22 could be processed by a computer 25.

A portion 26 of the jacket 10 is cut away from a segment of cable 2, exposing a region 28 of insulation 8. This exposed insulation region 28 is then irradiated by emissions 30 from the excitation source 12. The source 12 preferably outputs excitation of a single wavelength chosen to cause bulk fluorescence in the insulation under test. Preferably the source 12 is a commercially available laser unit (such as a 5 watt Argon laser). However source 12 may be a broad band emitter whose output is filtered to a single desired wavelength, or the like. Although the distance is not critical, for convenience, laser 12 preferably is located a few meters from the target region 28, an area of about 1 cm². The angle of incidence $\theta$ between the axis of laser 12 and the target region 28 is not critical, and any angle $\theta$ between about 90° and about 10° will suffice.

Although the laser source emissions 30 are essentially single wavelength, the inherent bulk fluorescence of the insulation region 28 causes a broad spectrum 32 of response radiation to be emitted from region 28. Applicant has discovered that for XLPE insulation, a laser wavelength of about 514.5 nm produces a very satisfactory response spectrum.

As explained by the Stokes shift, the fluorescing insulation region 28 transforms the laser emissions 30 into emitted radiation 32 of longer wavelength because energy losses are always present. Thus, in the preferred embodiment, where the laser emission 30 is about 514.5 nm (e.g. visibly green), the XLPE insulation region 28 absorbs these emissions and fluoresces with response spectrum emissions 32 having wavelengths from about 550 to about 750 nm (e.g., visibly yellow-orange).

The response spectrum radiation 32 is focussed by the lens 16 onto a double monochromator 18, preferably equipped with a photomultiplier tube 20 to provide gain. In the preferred embodiment, the lens 16 has a focal length of about 15 cm, while the double monochromator 18 is implemented with two 0.25 m monochromators arranged in tandem to reduce the deleterious effects of any laser radiation 30 scattered from the sample region 38. The photomultiplier tube 20 output is a signal proportional to the bulk fluorescence intensity. This output signal preferably is coupled to a commercially available photon counter 20 whose output is displayed on a chart recorder 24 (or similar device). Of course, other mechanisms for converting the bulk fluorescence emissions 32 into useful data representing intensity as a function of wavelength could be used instead of the described optical measurement system 14.

Figure 2:
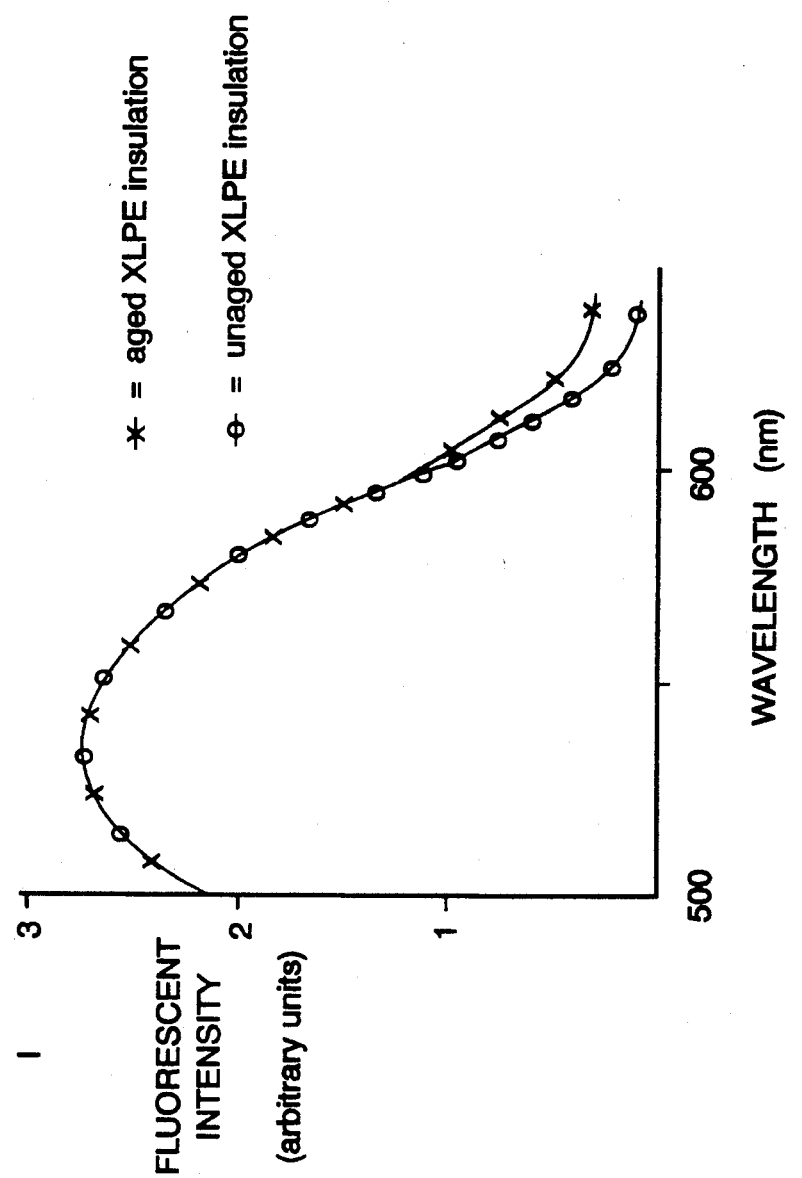
FIG. 2 is a graph demonstrating how transmission line insulation lifetime may be quantized using response spectrum intensities at two different wavelengths.

FIG. 2 is a graph of the intensity of the response spectrum emissions 32 for a region 38 of XLPE insulation, at various response spectrum wavelengths (both spectra being normalized for equal intensity at 580 nm). FIG. 2 represents the data available from the described optical measurement system 14, for aged and unaged XLPE insulation. The data in FIG. 2 are somewhat generalized in that no correction has been made for the wavelength response of the photomultiplier tube 20, or the monochromator system 18. Nonetheless, FIG. 2 demonstrates that at response spectrum emissions greater than about 600 nm, aged XLPE insulation fluoresces more than new XLPE insulation and provides a tool for quantizing insulation lifetime.

Applicant has discovered that for a laser emission of about 514.5 nm, intensity ratios at about $I_{550\text{-}600}/I_{600\text{-}750}$ discriminate between old insulation and new insulation, where I is intensity, and the subscript is the wavelength (nm) of the response spectrum emission at which the intensity is measured. For XLPE insulation, a ratio at $I_{580}/I_{650}$ appears to provide very good sensitivity.

The $I_{580}/I_{650}$ ratio is about 6.4 for new cable (i.e., cable with new insulation), and diminishes with age and environmental conditions to about 4.7 for failed or dead insulation. Laboratory aging to quarter-life results in a ratio of about 5.95, where the insulation is subjected to stress conditions of four times the rated voltage and to 60° C. (as opposed to the rated temperature of 45° C.) for 70 days. Half-life laboratory aging of insulation results in a ratio of about 5.3, where the insulation is subjected to the above described stress conditions for about 140 days. Failed insulation results in a ratio of about 4.7.

In field-aged XLPE insulation, the precise ratios correlating to age might differ somewhat from the laboratory data described above. Applicant anticipates that an $I_{580}/I_{650}$ ratio of less than about four will correlate with dead or failed insulation (e.g., 0% remaining lifetime).

Assume for simplicity of explanation however that the intensity ratios of field-aged XLPE insulation are essentially the same as the laboratory-aged data. Thus, if a given sample of insulation taken from an installed cable demonstrated an $I_{580}/I_{650}$ ratio of say about 5.0, it would be reasonable to predict that about 25% of the cable insulation lifetime remains. If records indicate that the cable in question was installed 30 years ago, then a ratio of about 5.0 would correlate with about 10 years of remaining life (e.g., 30 years of past life $\approx$ 75% of total lifetime).

In contrast to XLPE insulation, the nature of EPR insulation is that new insulation fluoresces with greater intensity than aged insulation. Thus, unlike XLPE insulation, the intensity ratio for EPR insulation increases with age. A ratio at about $I_{540}/I_{570}$ appears to provide good discrimination between aged and new EPR insulation. Preliminary testing with laboratory-aged EPR insulation suggests that an $I_{540}/I_{570}$ ratio less than about 1.0 correlates with new cable, and that a ratio greater than about 1.0 correlates with dead cable.

Although the preferred method has been described with reference to XLPE and EPR insulation, the present invention will provide quantization data for other insulation materials as well. However other insulation materials may require a different excitation wavelength to produce satisfactory fluorescence, and might require that the intensity ratio be determined at other wavelengths within the response spectrum emission. Nonetheless measurements of intensity ratios will discriminate between new and aged insulation, and provide a tool for quantizing remaining insulation lifetime. In practice, a correlation table of intensity ratios versus insulation lifetime for laboratory-aged and/or field-aged samples for the particular insulation material being used would be stored in a memory device for comparison with intensity ratio values based on current measurements.

Figure 3A:
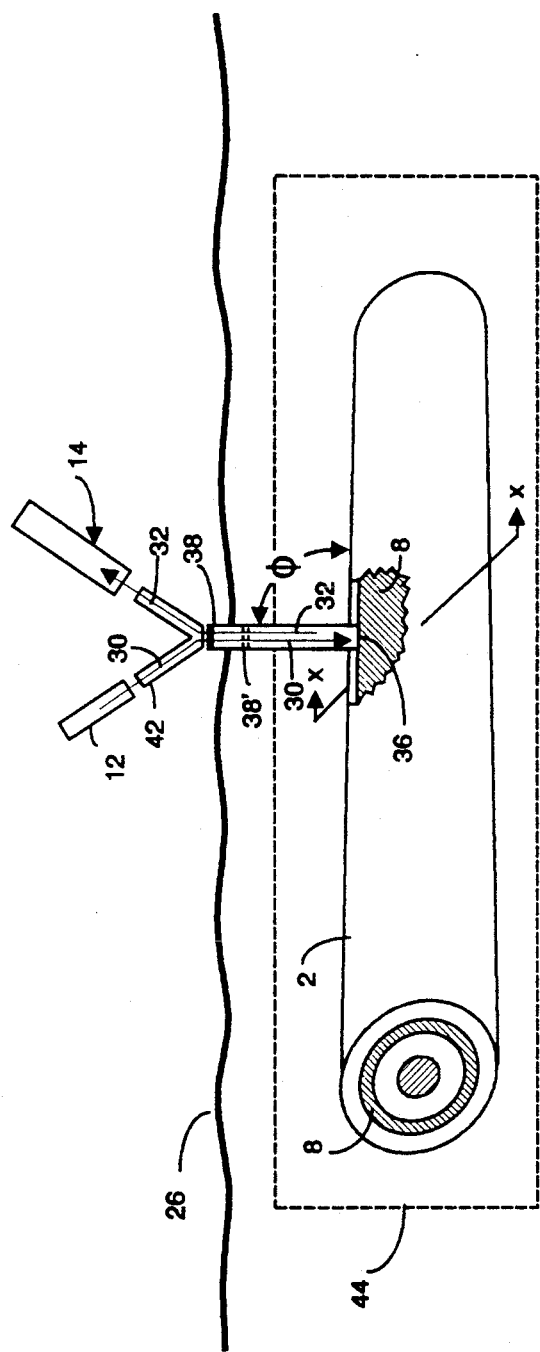
FIG. 3A depicts a transmission cable including a fiber optic sensor to facilitate quantization of the transmission cable insulation lifetime, according to the present invention.
Figure 3B:
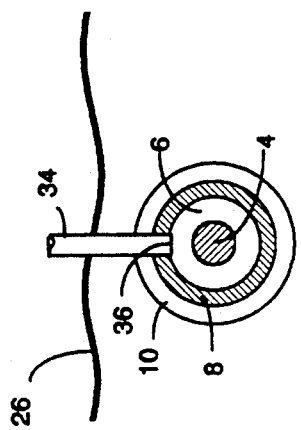
FIG. 3B is a cross-section of a portion of the cable depicted in FIG. 3A, taken along the section line X—X.

FIGS. 3A and 3B illustrate a preferred method of making the described measurements upon cable in situ. FIG. 3A shows a transmission cable 2 buried beneath the ground 26. The cable 2 includes a fiber optic sensor 34 whose first end 36 is embedded in the outer jacket 10 (when the cable is manufactured) sufficiently to just touch the insulation 8. (It is not desirable that end 36 itself be embedded within the insulation 8 as this would result in a weak spot.) Fiber optic sensor 34 has a second end 38 that preferably protrudes above the ground 26. Alternatively end 38 could remain somewhat underground (as indicated by end 38' shown in phantom) providing access to it could be obtained. In practice, sensor 34 is preferably a fiber optic cable (or equivalent mechanism for conveying optical radiation) whose length is a few meters or so, and whose cross-section diameter is about 0.5 mm to about 1 mm. Sensor 34 may emerge from cable 2 at an angle $\phi$ between about 10° and about 90°.

When it is desired to determine the remaining age of the insulation 8 within the cable 2, a laser or other excitation source 12 and optical measurement system 14 (as above described) are optically coupled to end 38 of the optic sensor 34 via a fiber optic section 42. Although section 42 is shown as generally "Y"-shaped, other configurations could be used as well. As before, the excitation source 8 emits radiation 30 at a wavelength suitable to produce fluorescence within insulation 8, which emitted radiation 30 is optically coupled via section 42 through the optic sensor 34 into insulation 8. The insulation 8 in turn emits a response spectrum 32, at least part of which is coupled via the optic sensor 34 and optic section 42 into the optical measurement system 14. As has already been described, intensity measurements are made at at least two wavelength within the emitted radiation spectrum and the intensity ratio determined. Using a table that correlates intensity ratios to estimated remaining insulation life for the type of insulation under test, a determination is made as to the remaining insulation life. Based upon this determination, a decision is then made whether to replace the cable 2.

Although field testing of insulation 8 has been described with regard to the buried cable 2 of FIG. 3A, cable 2 may be disposed in various environments as well. For example, cable 2 could be located within a nuclear reactor, a particle accelerator, or other high radiation environment 44 (indicated in phantom in FIG. 3A), with the optic sensor end 38 extending therefrom to permit safe measurements. In such a hostile environment, it may be both desirable and necessary to remotely monitor cable insulation lifetime.

Modifications and variations may be made to the disclosed embodiments without departing from the subject and spirit of the invention as defined by the following claims.

What is claimed is:

1. A method for quantizing the remaining life of insulation in a transmission cable, the method comprising the steps of:
   irradiating the insulation with excitation energy at a first wavelength causing the insulation to emit a bulk fluorescence spectrum containing at least second and third wavelengths longer than said first wavelength;
   measuring intensity of said bulk fluorescence spectrum at said second and third wavelengths;
   determining a ratio of the measured intensities at said second and third wavelengths;
   estimating from said ratio the remaining transmission cable insulation lifetime.

2. The method of claim 1, wherein said step of irradiating is performed by a laser.

3. The method of claim 1, wherein said first wavelength is about 514.5 nm.

4. The method of claim 1, wherein said ratio has a numerator representing bulk fluorescence intensity measured at a wavelength between about 550 nm to about 660 nm, and has a denominator representing bulk fluorescence intensity measured at a wavelength between about 600 nm and about 750 nm.

5. The method of claim 1, wherein for insulation including cross-linked polyethylene said ratio has a numerator representing bulk fluorescence intensity measured at a wavelength of about 580 nm, and has a denominator representing bulk fluorescence intensity measured at a wavelength of about 650 nm.

6. The method of claim 1, wherein for insulation including ethylene propylene rubber said ratio has a numerator representing bulk fluorescence intensity measured at a wavelength of about 540 nm, and has a denominator representing bulk fluorescence intensity measured at a wavelength of about 570 nm.

7. The method of claim 1, wherein said insulation includes a material selected from the group consisting of cross-linked polyethylene and ethylene propylene rubber.

8. The method of claim 1, wherein:
   said step of irradiating includes transmitting said excitation energy to said insulation via an optical fiber cable, and said measuring step includes transmitting at least a portion of said bulk fluorescence to an optical measurement system via said optical fiber cable.

9. The method of claim 8, wherein said transmission cable is disposed underground, said method including:
   said optical fiber cable communicating said excitation energy from a location above ground to said insulation, and
   said optical fiber cable furthermore communicating said bulk fluorescence from said insulation to said location above ground.

10. The method of claim 8, wherein said transmission cable is disposed in a radiation environment, said method including:

said optical fiber cable communicating said excitation energy from a location external to said radiation environment to said insulation, and said optical fiber cable furthermore communicating said bulk fluorescence from said insulation to said location external to said radiation environment.

11. The method of claim 8, wherein said estimating step includes comparing said ratio of measured intensities with a set of prerecorded intensity ratios and corresponding insulation lifetime values.

12. A system for testing insulation deterioration in a transmission cable, comprising:

a transmission cable including a length of electrically conductive line having a layer of insulation axially surrounding said line and an outer protective jacket axially surrounding said layer of insulation;

an optical source that produces an optical excitation signal;

a length of fiber optic cable having a first end embedded in said outer protective jacket so as to contact said layer of insulation and a second end coupled to said optical source, wherein said optical excitation signal is directed to said insulation, thereby producing bulk fluorescence in said layer of insulation; and an optical measurement system, coupled to said second end of said fiber optic cable, that measures intensity of said bulk fluorescence at at least two wavelengths.

13. The system of claim 12, wherein said optical measurement system includes means for determining an intensity ratio of said at least two wavelengths;

wherein said intensity ratio is indicative of remaining transmission cable insulation lifetime.

14. The system of claim 12, wherein said electrically conductive line defines a longitudinal axis of the transmission cable, and said first end of said fiber optic cable is embedded within said outer protective jacket such that said length of fiber optic cable protrudes therefrom at an angle between about 10° and about 90° relative to said longitudinal axis.

* * * * *